(12) United States Patent
Nichols et al.

(10) Patent No.: US 9,880,184 B2
(45) Date of Patent: Jan. 30, 2018

(54) PIPETTOR SYSTEM

(71) Applicant: HighRes Biosolutions, Inc., Woburn, MA (US)

(72) Inventors: Michael Nichols, Newburyport, MA (US); Louis J. Guarracina, Newburyport, MA (US)

(73) Assignee: HighRes Biosolutions, Inc., Beverly, MA (US)

( * ) Notice: Subject to any disclaimer, the term of this patent is extended or adjusted under 35 U.S.C. 154(b) by 0 days.

(21) Appl. No.: 15/454,122

(22) Filed: Mar. 9, 2017

(65) Prior Publication Data
US 2017/0176483 A1 Jun. 22, 2017

Related U.S. Application Data

(63) Continuation of application No. 14/636,962, filed on Mar. 3, 2015, now Pat. No. 9,623,405.

(51) Int. Cl.
*B01L 3/02* (2006.01)
*G01N 35/00* (2006.01)
*G01N 35/10* (2006.01)

(52) U.S. Cl.
CPC ..... *G01N 35/1072* (2013.01); *G01N 35/0099* (2013.01); *G01N 35/1011* (2013.01); *G01N 2035/1076* (2013.01)

(58) Field of Classification Search
CPC ........... G01N 35/1002; G01N 35/1065; G01N 35/04; G01N 2035/0425; G01N 2035/0439; G01N 2035/0474; B01L 3/0227
See application file for complete search history.

(56) References Cited

U.S. PATENT DOCUMENTS

| 5,055,263 A * | 10/1991 | Meltzer | G01N 35/1072 422/561 |
| 5,306,510 A * | 4/1994 | Meltzer | G01N 35/1072 422/561 |
| 5,512,247 A * | 4/1996 | Bonacina | G01B 7/282 324/519 |
| 5,948,359 A * | 9/1999 | Kalra | G01N 1/312 422/510 |
| 5,958,342 A * | 9/1999 | Gamble | B01J 19/0046 347/1 |

(Continued)

OTHER PUBLICATIONS

PCT International Search Report for International Application No. PCT/US2016020326, dated Jun. 13, 2016, 11 pages.

(Continued)

*Primary Examiner* — Brian R Gordon
(74) *Attorney, Agent, or Firm* — Perman & Green, LLP

(57) ABSTRACT

Various embodiments include a system having: a pipetting chamber; a set of pipettor cartridges docked in the pipetting chamber; a gantry system mounted on a ceiling within the pipetting chamber, the gantry system including: at least one stationary track aligned in a first direction; and a movable track aligned in a second direction distinct from the first direction, the movable track coupled to the at least one stationary track; and a carrier configured to transport each of the set of pipettor cartridges to a pipetting location within the pipetting chamber, the carrier configured to move each pipettor cartridge in a third direction perpendicular to both the first and second directions.

42 Claims, 19 Drawing Sheets

(56) References Cited

U.S. PATENT DOCUMENTS

| | | | |
|---|---|---|---|
| 6,299,840 B1* | 10/2001 | Watanabe | G01N 35/0099 |
| | | | 422/50 |
| 6,325,114 B1 | 12/2001 | Bevirt et al. | |
| 7,858,041 B2* | 12/2010 | Muraishi | B01L 3/021 |
| | | | 422/511 |
| 7,968,060 B2 | 6/2011 | Van Tuyl | |
| 8,211,301 B2 | 7/2012 | Safar et al. | |
| 8,282,895 B2* | 10/2012 | Miller | G01N 35/1002 |
| | | | 137/259 |
| 8,404,492 B2 | 3/2013 | Baldassari et al. | |
| 8,638,509 B2 | 1/2014 | Blasenheim et al. | |
| 8,865,474 B2 | 10/2014 | Paschetto et al. | |
| 9,028,754 B2* | 5/2015 | Winter | G01N 1/42 |
| | | | 422/560 |
| 9,623,405 B2* | 4/2017 | Nichols | B01L 3/0227 |
| 2003/0215357 A1 | 11/2003 | Malterer et al. | |
| 2004/0081583 A1 | 4/2004 | Berndt et al. | |
| 2004/0096360 A1* | 5/2004 | Toi | G01N 35/1067 |
| | | | 422/63 |
| 2006/0138409 A1 | 8/2006 | Chang et al. | |
| 2010/0105074 A1 | 4/2010 | Covey et al. | |
| 2012/0291872 A1 | 11/2012 | Brady et al. | |
| 2013/0280145 A1 | 10/2013 | West et al. | |
| 2013/0295597 A1 | 11/2013 | DeWitte et al. | |
| 2014/0045186 A1 | 2/2014 | Gubatayao et al. | |
| 2014/0260696 A1 | 9/2014 | Criswell | |

OTHER PUBLICATIONS

Office Action for U.S. Appl. No. 14/636,962, dated Aug. 11, 2016, 13 pages.
Notice of Allowance for U.S. Appl. No. 14/636,962, dated Dec. 9, 2016, 11 pages.

* cited by examiner

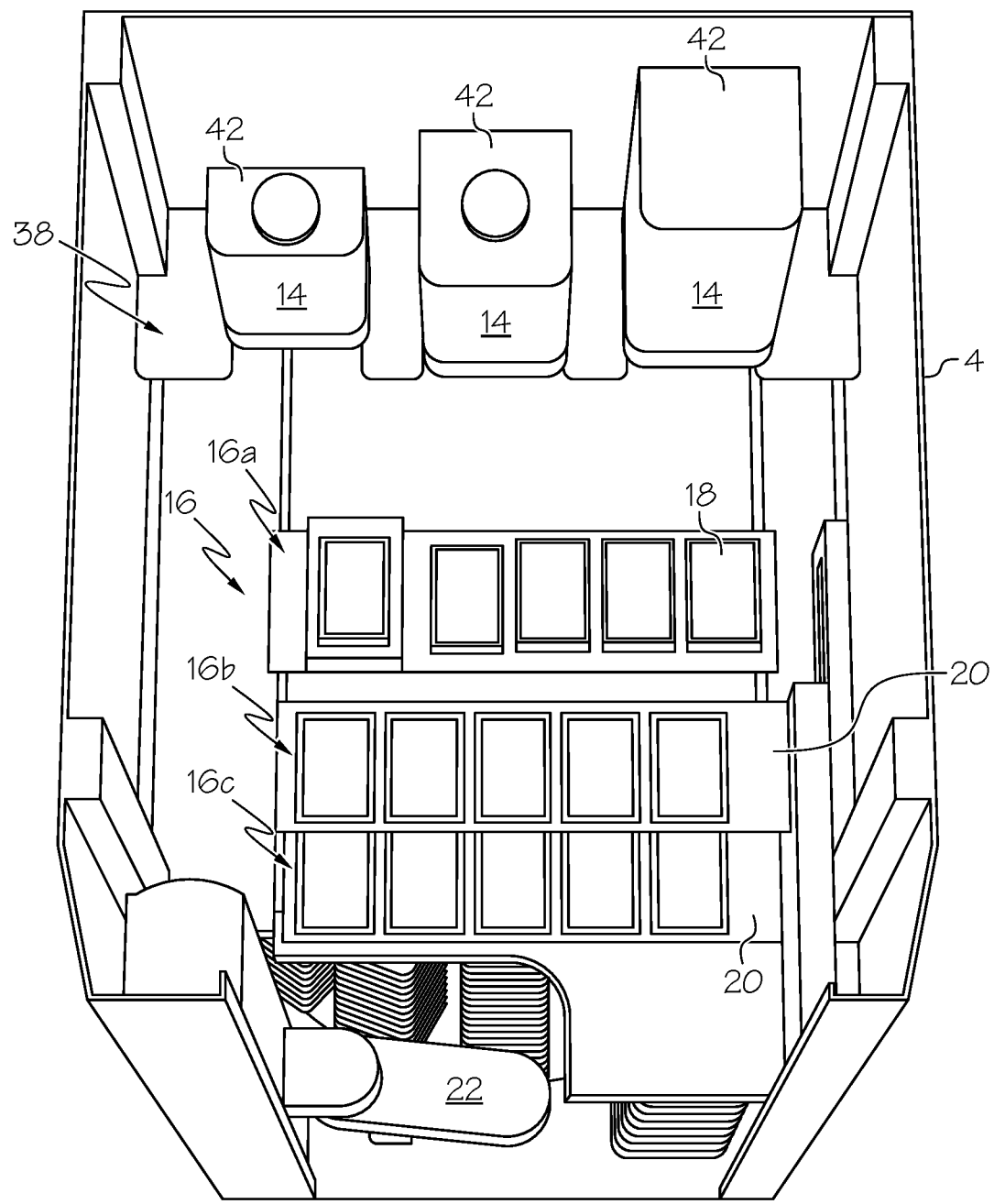
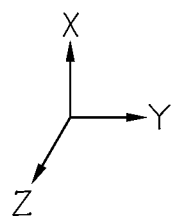
FIG. 6

PIPETTOR SYSTEM

CROSS-REFERENCE TO RELATED APPLICATION

This application is a continuation of U.S. patent application Ser. No. 14/636,962, filed Mar. 3, 2015, which received a Notice of Allowance on Dec. 9, 2016, and is hereby incorporated by reference in its entirety.

FIELD

The subject matter disclosed herein relates to life sciences equipment. More particularly, the subject matter disclosed herein relates to pipetting equipment for use in the life sciences industry.

BACKGROUND

Pipettors, also referred to as chemical droppers, are laboratory tools commonly used in the life sciences industry to dispense a volume of liquid. As life sciences equipment has advanced, many pipettors have been integrated into automated systems. While these automated systems have improved the accuracy and control of pipetting procedures, these conventional automated systems can be less than dynamic in their ability to handle distinct pipetting procedures.

BRIEF DESCRIPTION

Various embodiments include a system having: a pipetting chamber; a set of pipettor cartridges docked in the pipetting chamber; a gantry system mounted on a ceiling within the pipetting chamber, the gantry system including: at least one stationary track aligned in a first direction; and a movable track aligned in a second direction distinct from the first direction, the movable track coupled to the at least one stationary track; and a carrier configured to transport each of the set of pipettor cartridges to a pipetting location within the pipetting chamber, the carrier configured to move each pipettor cartridge in a third direction perpendicular to both the first and second directions.

A first aspect includes a system having: a pipetting chamber; a set of pipettor cartridges docked in the pipetting chamber; a gantry system mounted on a ceiling within the pipetting chamber, the gantry system including: at least one stationary track aligned in a first direction; and a movable track aligned in a second direction distinct from the first direction, the movable track coupled to the at least one stationary track; and a carrier configured to transport each of the set of pipettor cartridges to a pipetting location within the pipetting chamber, the carrier configured to move each pipettor cartridge in a third direction perpendicular to both the first and second directions.

A second aspect includes a system having: a pipetting chamber having a ceiling within the pipetting chamber; a set of pipettor cartridges docked on the ceiling within the pipetting chamber; a gantry system mounted on the ceiling within the pipetting chamber, the gantry system including: at least one stationary track aligned in a first direction; and a movable track aligned in a second direction distinct from the first direction, the movable track coupled to the at least one stationary track; and a carrier configured to transport each of the set of pipettor cartridges to a pipetting location within the pipetting chamber, the carrier configured to move each pipettor cartridge in a third direction perpendicular to both the first and second directions; and a control system coupled with the pipetting chamber, the control system for controlling movement of the carrier along the first direction, the second direction and the third direction.

A third aspect includes a pipetting chamber having a ceiling within the pipetting chamber; a set of pipettor cartridges docked on the ceiling within the pipetting chamber; a gantry system mounted on the ceiling within the pipetting chamber, the gantry system including: at least one stationary track aligned in a first direction; and a movable track aligned in a second direction distinct from the first direction, the movable track coupled to the at least one stationary track; and a carrier configured to transport each of the set of pipettor cartridges to a pipetting location within the pipetting chamber, the carrier configured to move each pipettor cartridge in a third direction perpendicular to both the first and second directions, wherein the carrier is further configured to move completely circumferentially about the set of pipettor cartridges docked on the ceiling; and a control system coupled with the pipetting chamber, the control system for controlling movement of the carrier along the first direction, the second direction and the third direction.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 6 shows a cut-away plan view of one configuration of an interior of pipetting chamber from FIGS. 1-5 according to various embodiments.

Figure 1:
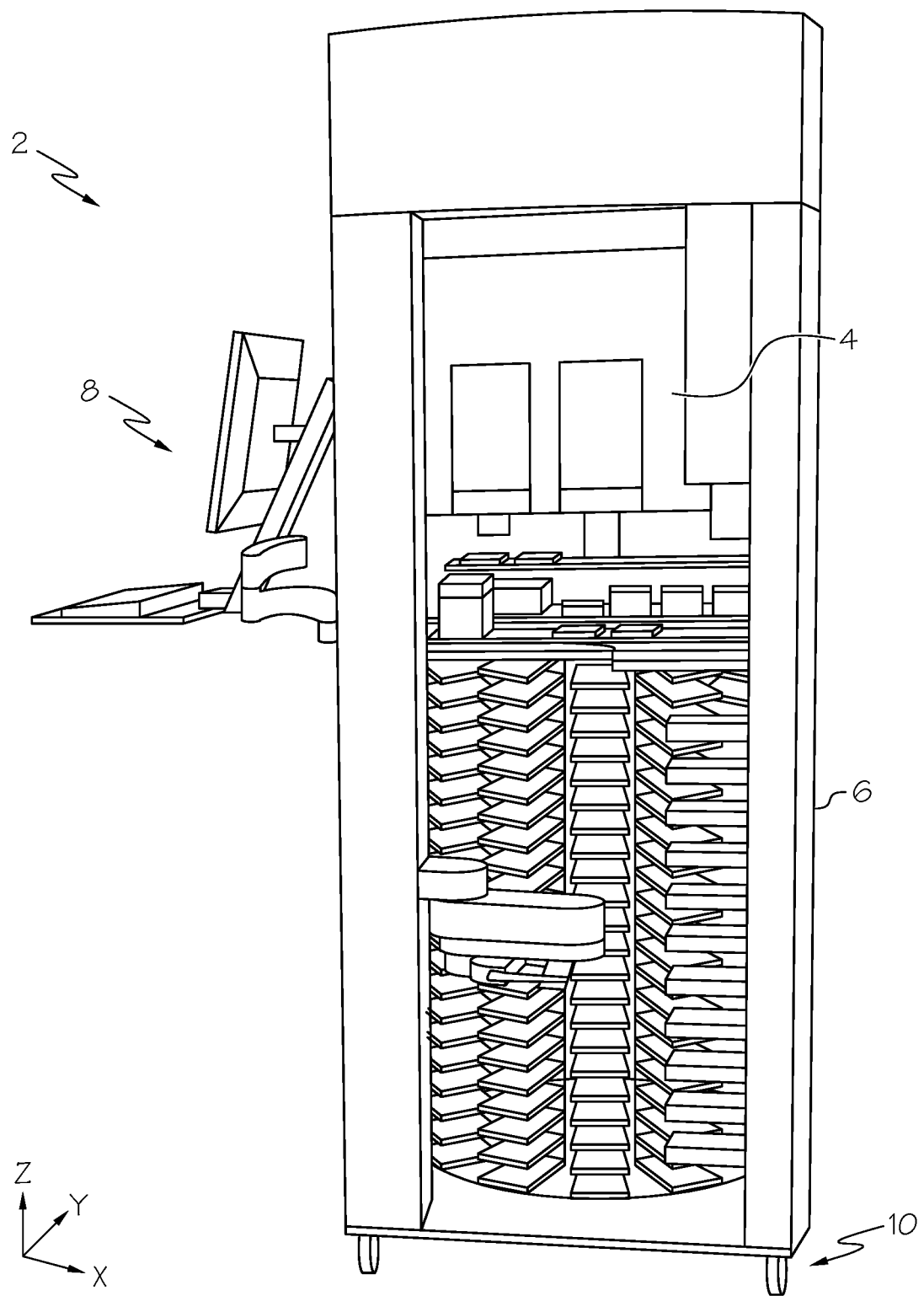
FIGS. 1-5 shows respective side perspective views of a system according to various embodiments.
Figure 2:
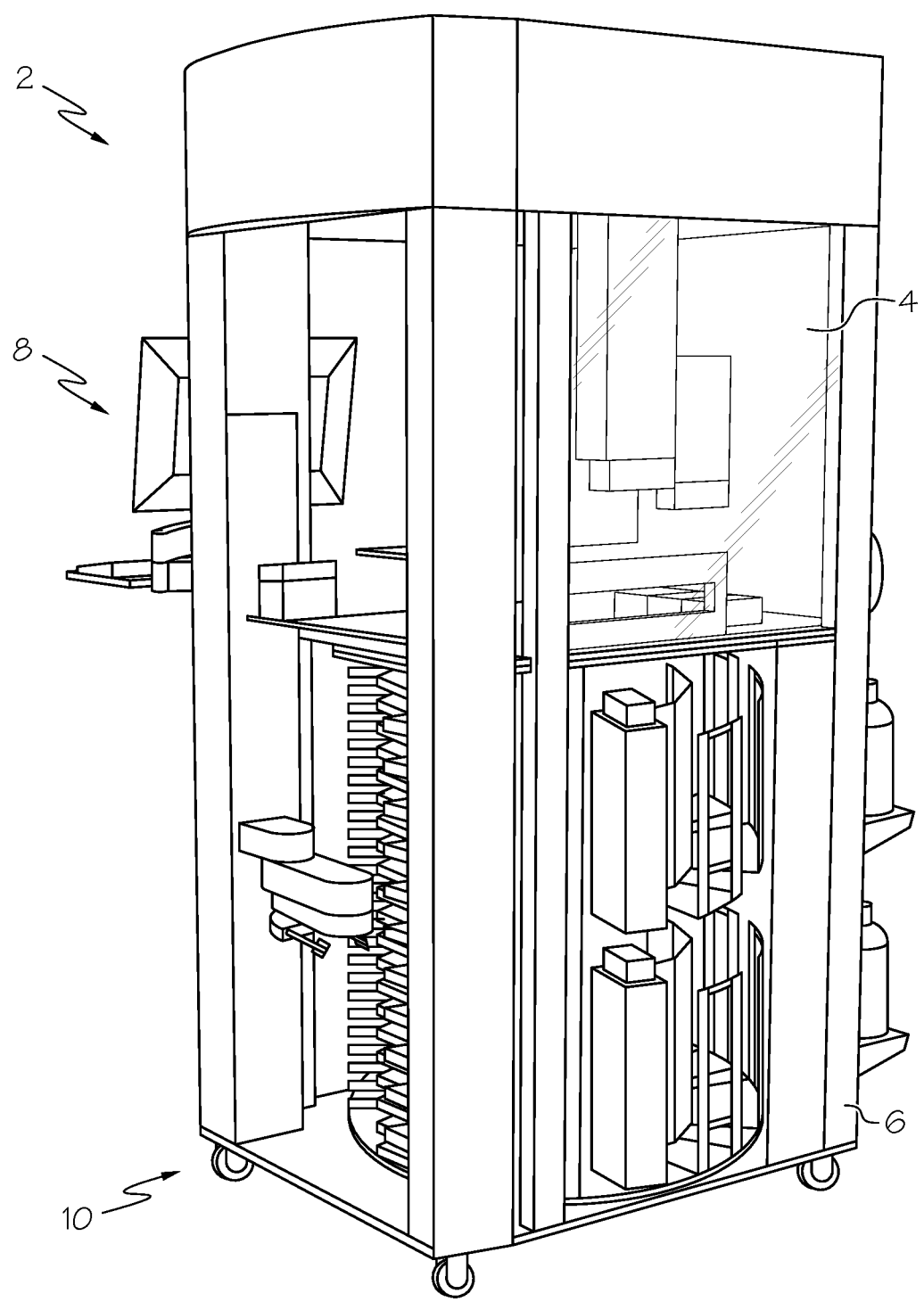
Figure 3:
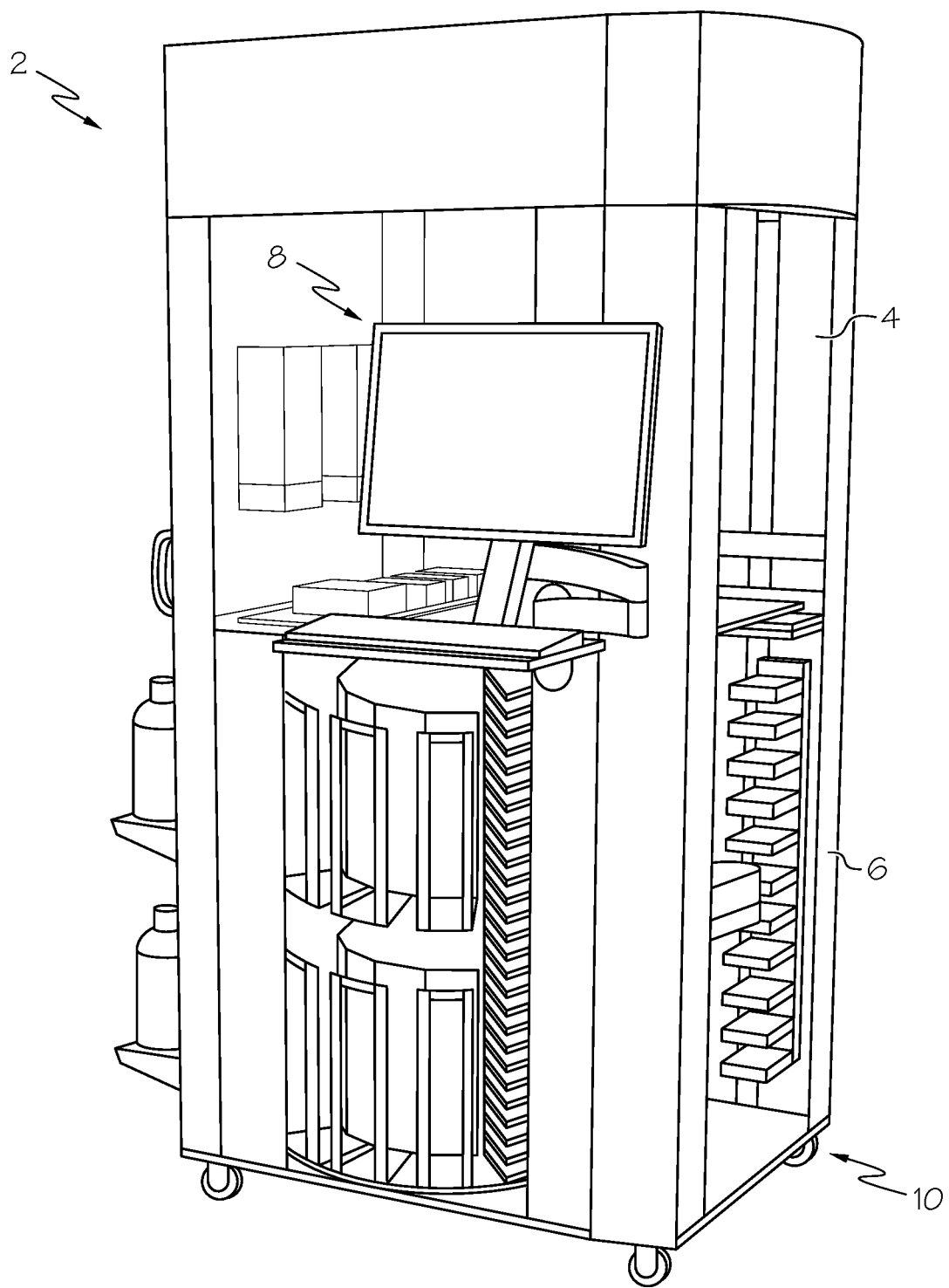

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION

As indicated above, the subject matter disclosed herein relates to life sciences equipment. More particularly, the subject matter disclosed herein relates to pipetting equipment for use in the life sciences industry.

In contrast to conventional pipettor systems, various embodiments include a pipettor system having a gantry configured to move in the X direction, Y direction and Z direction. In some cases, the gantry can include a first sliding rail coupled to a carrier, and at least one (e.g., two) fixed rail, which with the sliding rail is configured to traverse. The carrier may also be configured to move along the sliding rail. A set of docked, movable pipettor cartridges can be located within range of the carrier, which can selectively remove a cartridge from its dock, and transport the cartridge to a pipetting location. The pipetting location can be below (in Z direction) the docking location in some embodiments. In various embodiments, the pipetting location can be located on a pipetting platform, which may also be movable in the X-Y-Z direction. In various embodiments, the docking location of the pipettor cartridges is an overhead docking location. In some particular embodiments, the carrier can rotate around its own central axis to pick up, dock, or facilitate pipetting. The systems disclosed according to various embodiments are configured to effectively execute a variety of pipetting operations within the pipetting chamber without manual intervention.

In the following description, reference is made to the accompanying drawings that form a part thereof, and in which is shown by way of illustration specific example embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Figure 4:
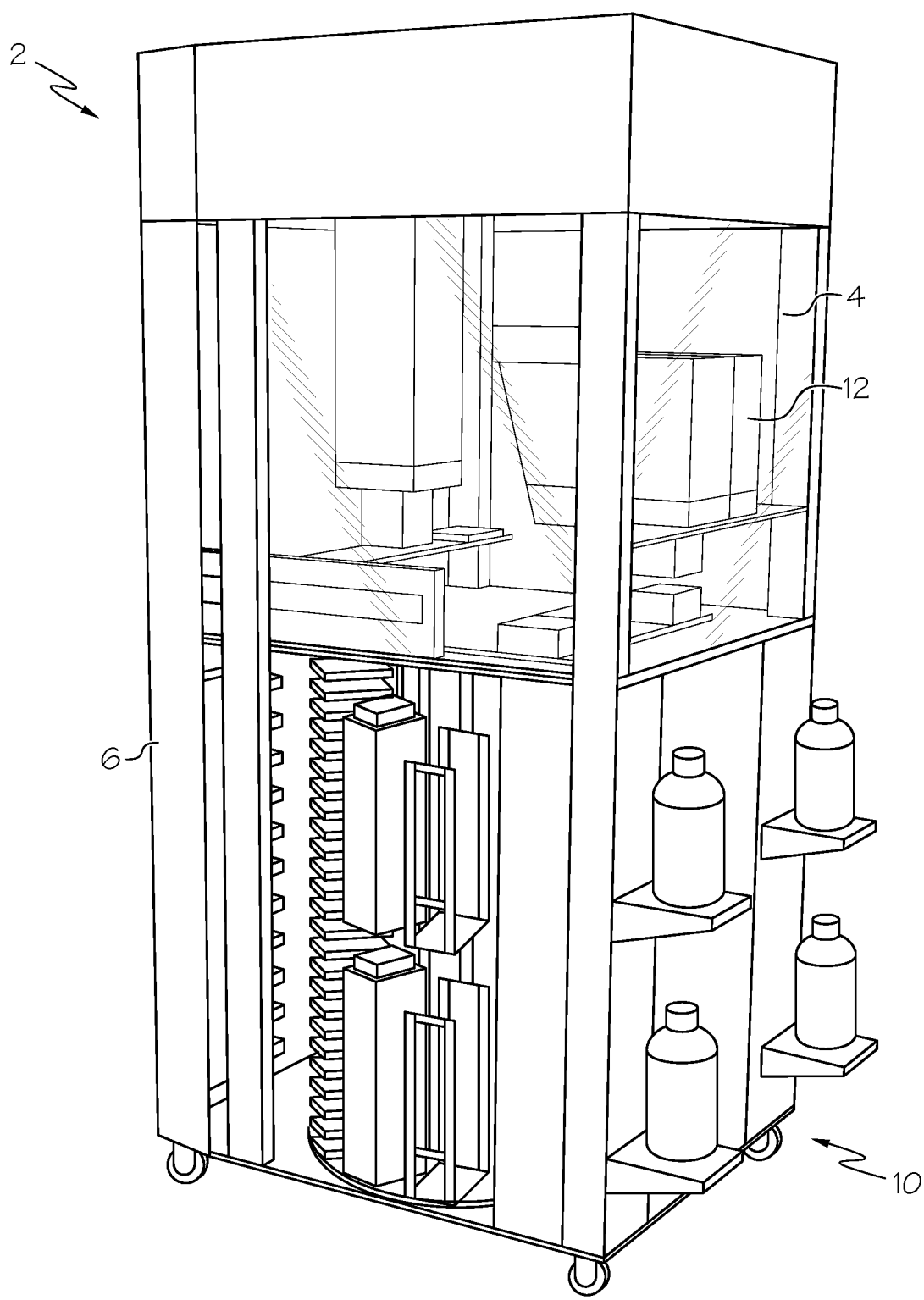
Figure 5:
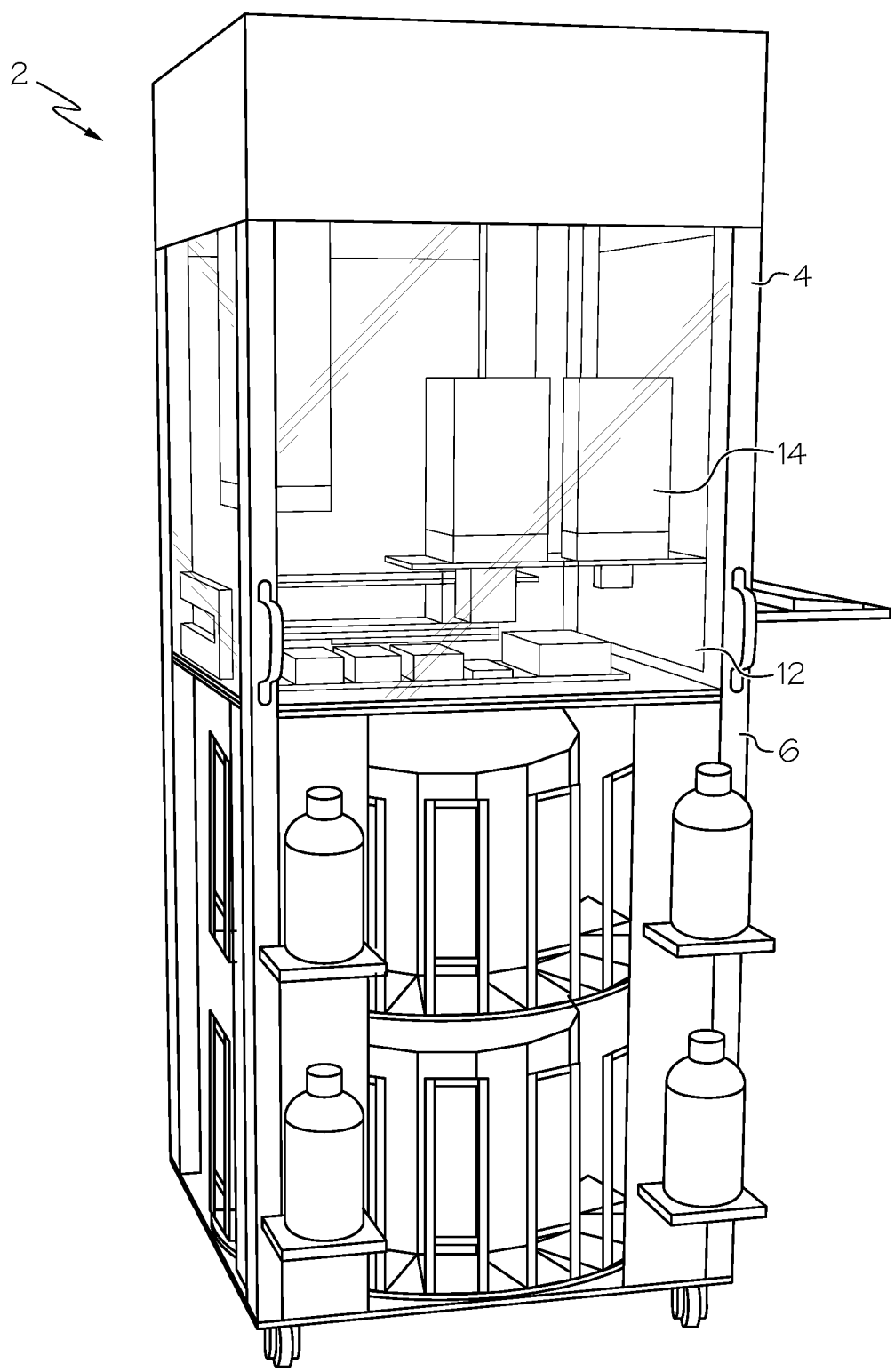

FIGS. 1-5 show respective side perspective views of a system 2 according to various embodiments. As shown, the system 2 can include a pipetting chamber 4, and in some embodiments, the system 2 can further include a storage chamber 6 coupled with the pipetting chamber 4. According to various embodiments, the system 2 can further include a control system 8, e.g., a computerized control system, as described further herein. As further described with respect to the additional FIGURES, in some embodiments, the pipetting chamber 4 is separated from the storage chamber 6, such that the pipetting chamber 4 can act as an independent pipetting chamber. However, in other embodiments, the pipetting chamber 4 and storage chamber 6 are coupled and may be connected with (integrally or separately) a cart system 10 (e.g., a set of wheels, rollers, track, etc.). FIG. 4 illustrates a set of doors 12, which can provide access to the pipetting chamber 4, which is otherwise sealed from the ambient environment when the doors 12 are closed. It is understood that the storage chamber 6 may be similarly sealed from the ambient environment. Various components are labeled in FIGS. 1-5 which are shown and described in greater detail according to additional FIGURES. It is understood that multiple figures are referenced for clarity of illustration and explanation.

FIG. 6 shows a cut-away plan view of one configuration of an interior of pipetting chamber 4 according to various embodiments. As shown, the pipetting chamber 4 can contain a set of pipettor cartridges 14 docked in the pipetting chamber 4 (e.g., at dock location 16). The pipetting chamber 4 can further include at least one tray dock 16 holding a set (at least one) of pipetting trays 18. In various embodiments, as shown in FIG. 6, the tray dock 16 includes distinct tray docks 16a, 16b, 16c, which include at least one static nest position 18 (tray dock 16a at the time of this depiction), and at least one dynamic nest position 20 (tray docks 16b, 16c, at the time of this depiction). In some cases, the dynamic nest positions are at distinct heights (Z-direction) within the pipetting chamber 4, and are adjustable horizontally (X-direction) within the pipetting chamber 4. In various embodiments, one tray dock 16 can be loaded/unloaded onto/off-of the static nest position 18 from one of the dynamic nest positions 20 by an arm 22, which is movable in the X-direction, Y-direction and Z-direction.

Figure 7:
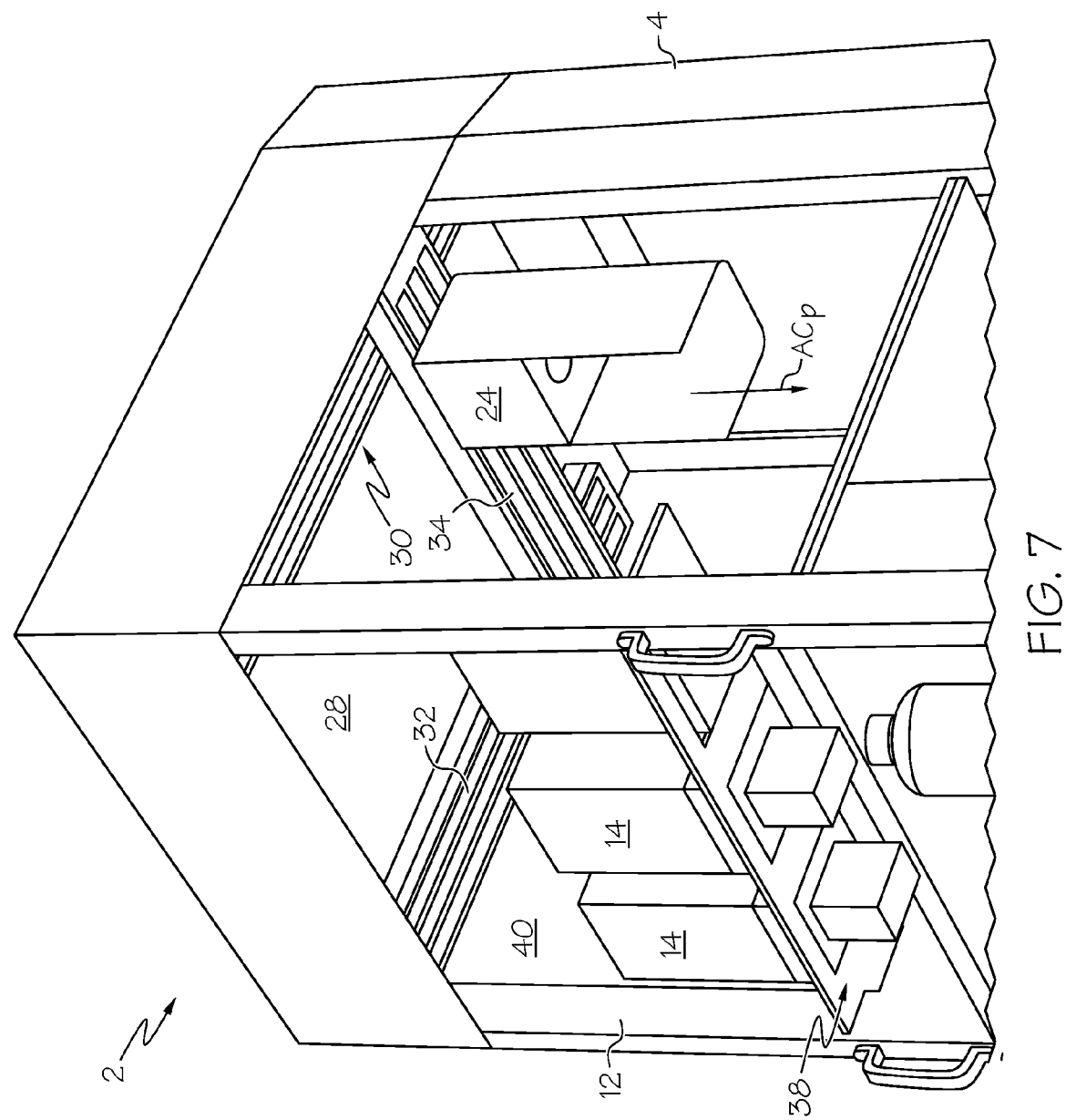
FIG. 7 shows an underneath perspective view of a portion of the system of FIGS. 1-5, including in particular the pipetting chamber, according to various embodiments.

FIG. 7 shows an underneath perspective view of a portion of the system 2, including in particular the pipetting chamber 4. As shown in this embodiment, the pipetting chamber 4 can further include a carrier 24 which in various embodiments, is movably coupled to the ceiling 28 within the pipetting chamber 4, and in various embodiments, is coupled to the ceiling 28 via a gantry system 30. The gantry system 30 can be mounted on the ceiling 28, and include at least two distinct tracks, e.g., at least one stationary track 32 (two shown) aligned in a first direction (X-direction), and a movable track 34 aligned in a second direction (Y-direction) distinct from the first direction. The movable track 34 can be coupled to the stationary track(s) 32, e.g., by complementary track integration, meaning that the movable track 34 can move within the stationary track(s) 32, such that the movable track 34 remains parallel with the stationary track(s) 32. In various embodiments, the at least one stationary track 32 includes two distinct stationary tracks 32 aligned in parallel, where the two distinct stationary tracks 32 are aligned perpendicular to the movable track 34.

As shown in FIG. 7 (as well as FIGS. 13-15 and 18), the carrier 24 is configured to transport each of the set of pipettor cartridges 14 to a pipetting location, e.g., a location of at least one of the pipetting trays 18 within a tray dock 16 in the pipetting chamber 4. In various embodiments, as described herein, the carrier 24 can be configured to move each pipettor cartridge 14 in a third direction (Z-direction) perpendicular to both the first (X) and second (Y) directions. According to various embodiments, the carrier 24 can be configured to rotate about its primary axis ($A_{Cp}$) such that the carrier 24 can circumferentially navigate about one or more of the pipettor cartridges 14. Further, the carrier 24, when engaged with a pipettor cartridge 14, can rotate that pipettor cartridge 14 about the primary axis of the carrier 24 ($A_{Cp}$), which can facilitate in pipetting operations, as well as in loading and/or unloading of pipettor cartridges.

Figure 8:
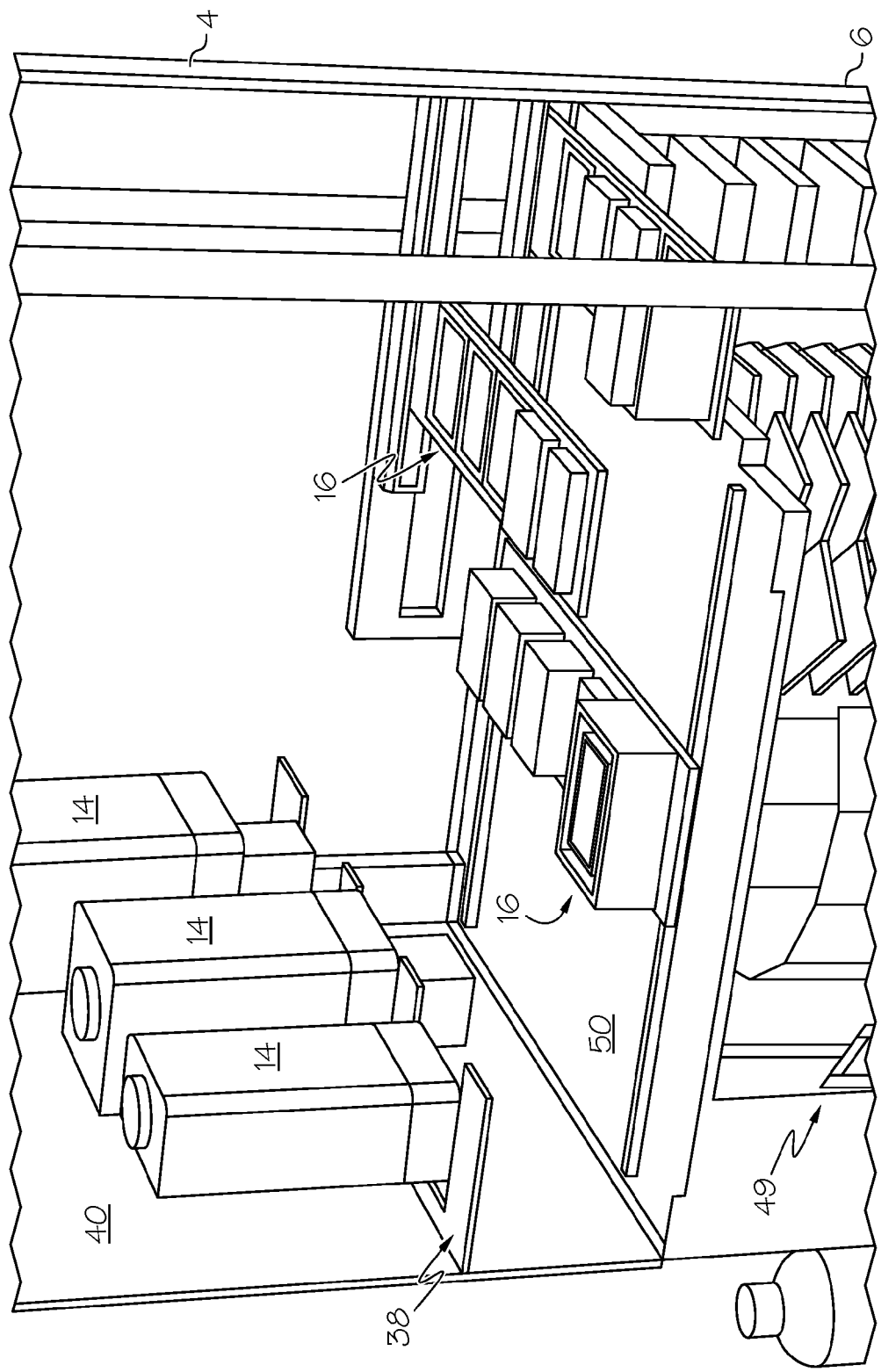
FIG. 8 shows a cut-away perspective view of a system according to various embodiments.

In some embodiments, for example, as shown in FIGS. 7 and 8, the set of pipettor cartridges 14 are docked in a docking station 38 coupled to a sidewall 40 of the interior of the pipetting chamber 4. The docking station 38 can be located in such a manner that the carrier 24 can engage the pipetting cartridges 14 from a top surface 42 of the pipettor cartridges 14. However, in other embodiments (e.g., as shown in the perspective views of FIGS. 14-17), the set of pipetting cartridges 14 are docked in a docking station 38 coupled to the ceiling 28 of the pipetting chamber 4, such that the pipettor cartridges 14 hang from overhead mounts 44 (FIG. 15) in the pipetting chamber 4. In these embodiments, the carrier 24 can be configured to engage a side of the pipettor cartridges 14 (FIG. 14, FIG. 15) and transport the cartridges 14 to/from the pipetting trays 18 and docking station 38.

Figure 9:
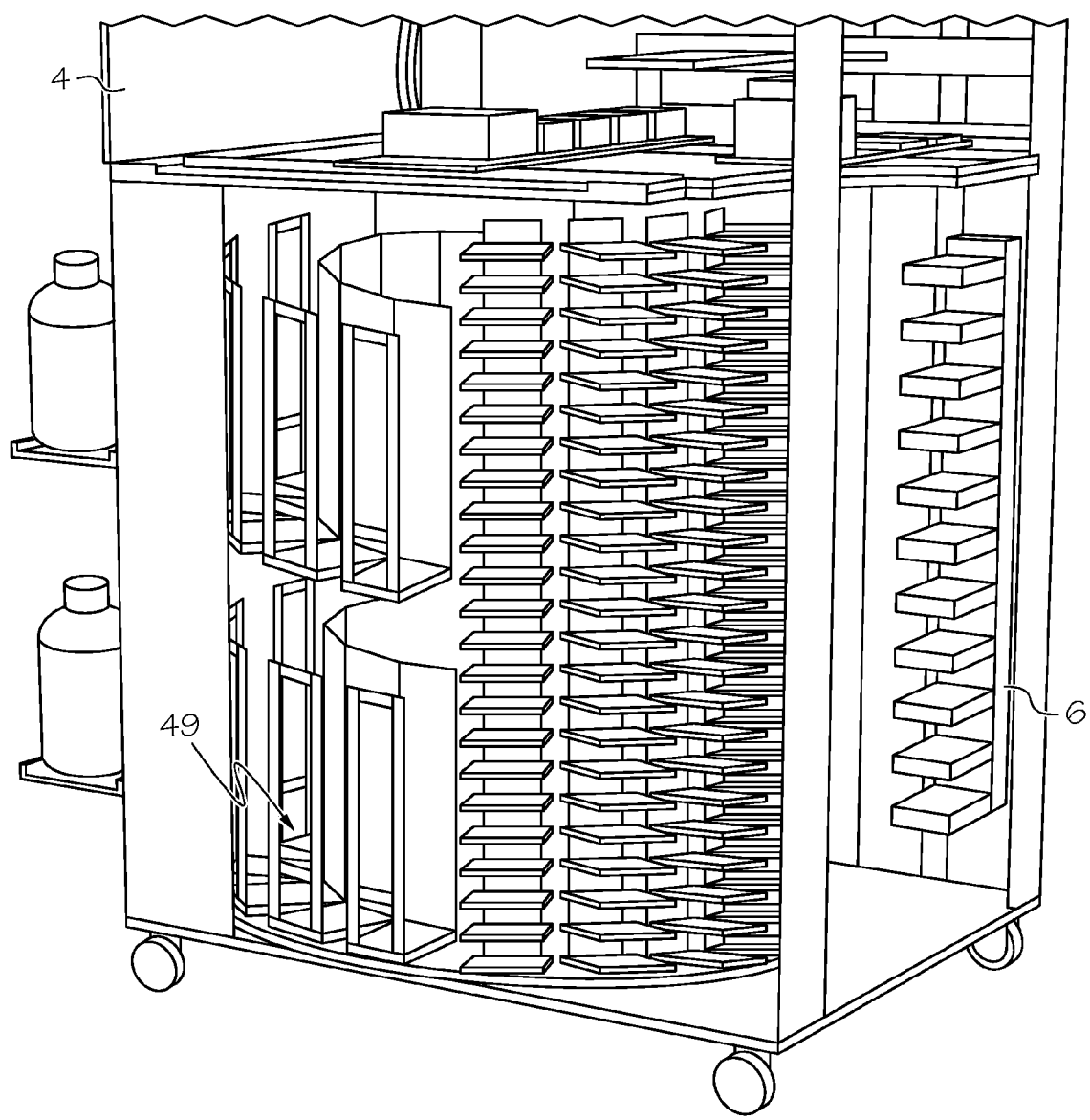
FIGS. 9-11 show respective cut-away perspective views of a storage chamber according to various embodiments.
Figure 10:
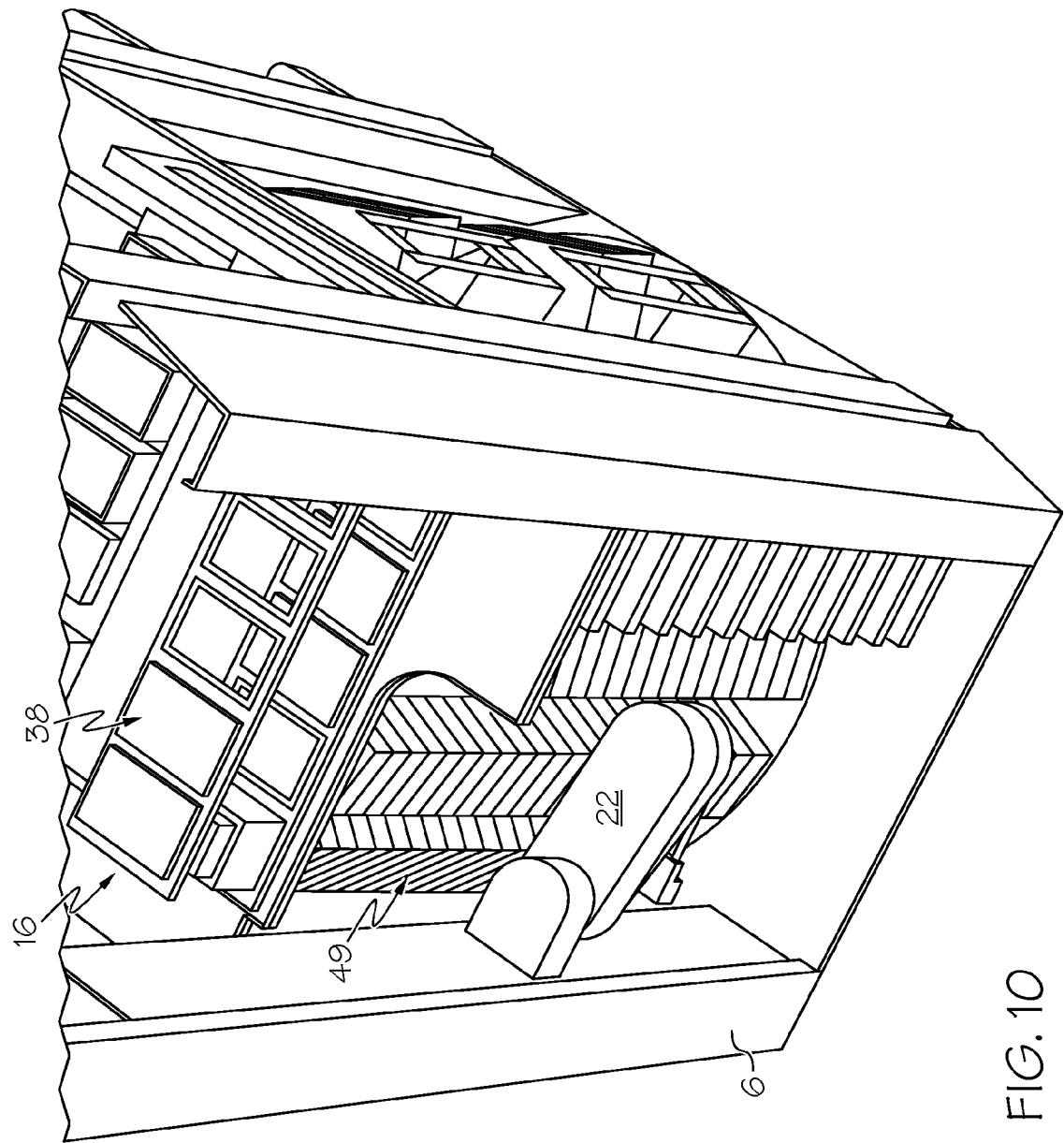
Figure 11:
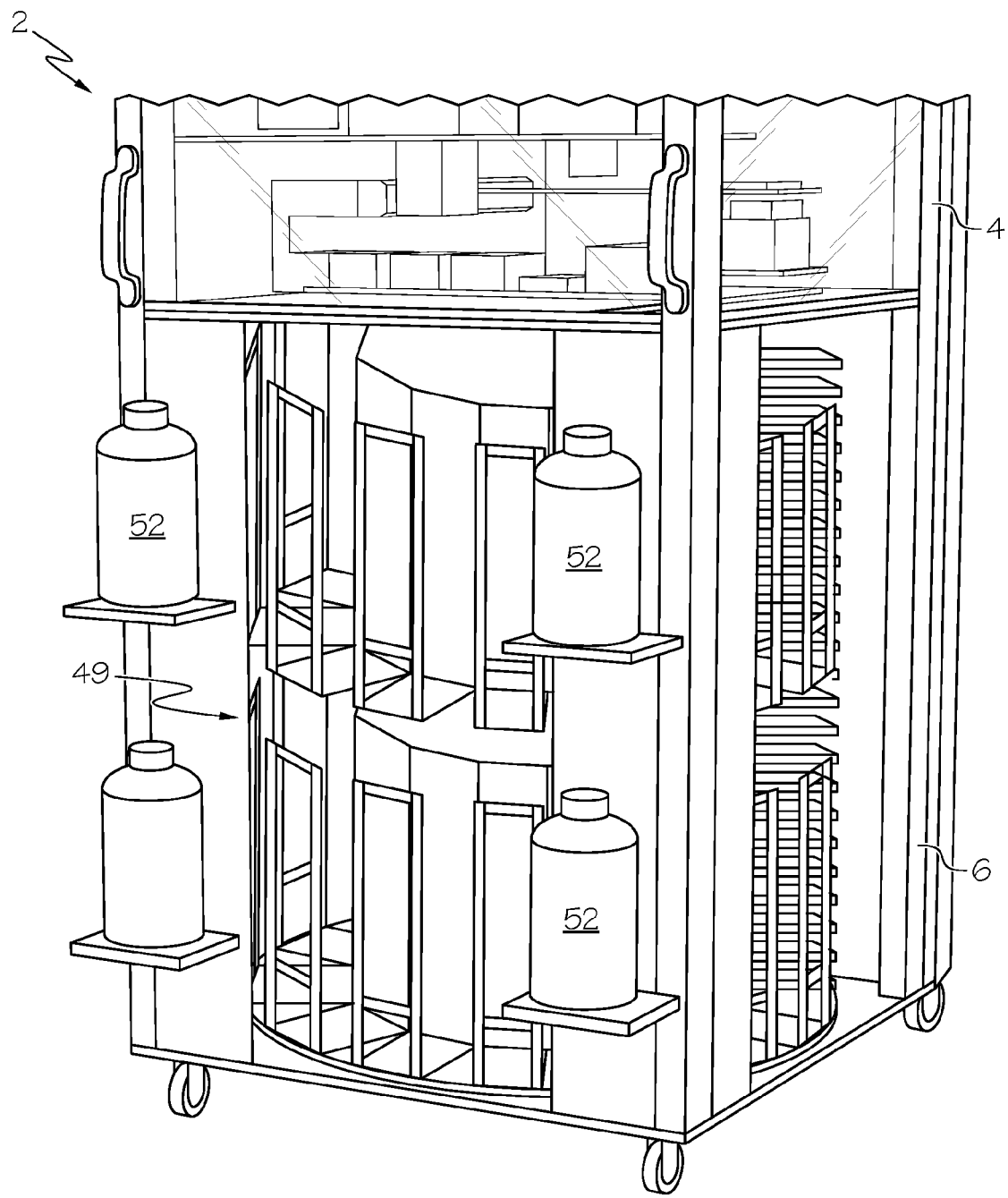

According to various embodiments, as illustrated in the cut-away perspective view of the system 2 in FIG. 8, the storage chamber 6 and the pipetting chamber 4 may be fluidly connected (such that a fluid, e.g., air, water, etc. may pass between) such that the pipetting trays 18 can be passed between the pipetting chamber 4 and the storage chamber 6 (and vice versa) via a lift system traversing the floor 50 of the pipetting chamber 4. The storage chamber 6 can store pipetting trays 18 when not in use in the pipetting chamber 4. The cut-away perspective views in FIGS. 9, 10 and 11 show additional features of the storage chamber 6, including a storage carousel 49 and robotic arm 22 configured to move pipetting trays 18 along the Z direction between the pipetting chamber 4 and the storage chamber 6, and further configured to move pipetting trays 18 in the X and Y directions within each of the pipetting chamber and the storage chamber 6.

Figure 13:
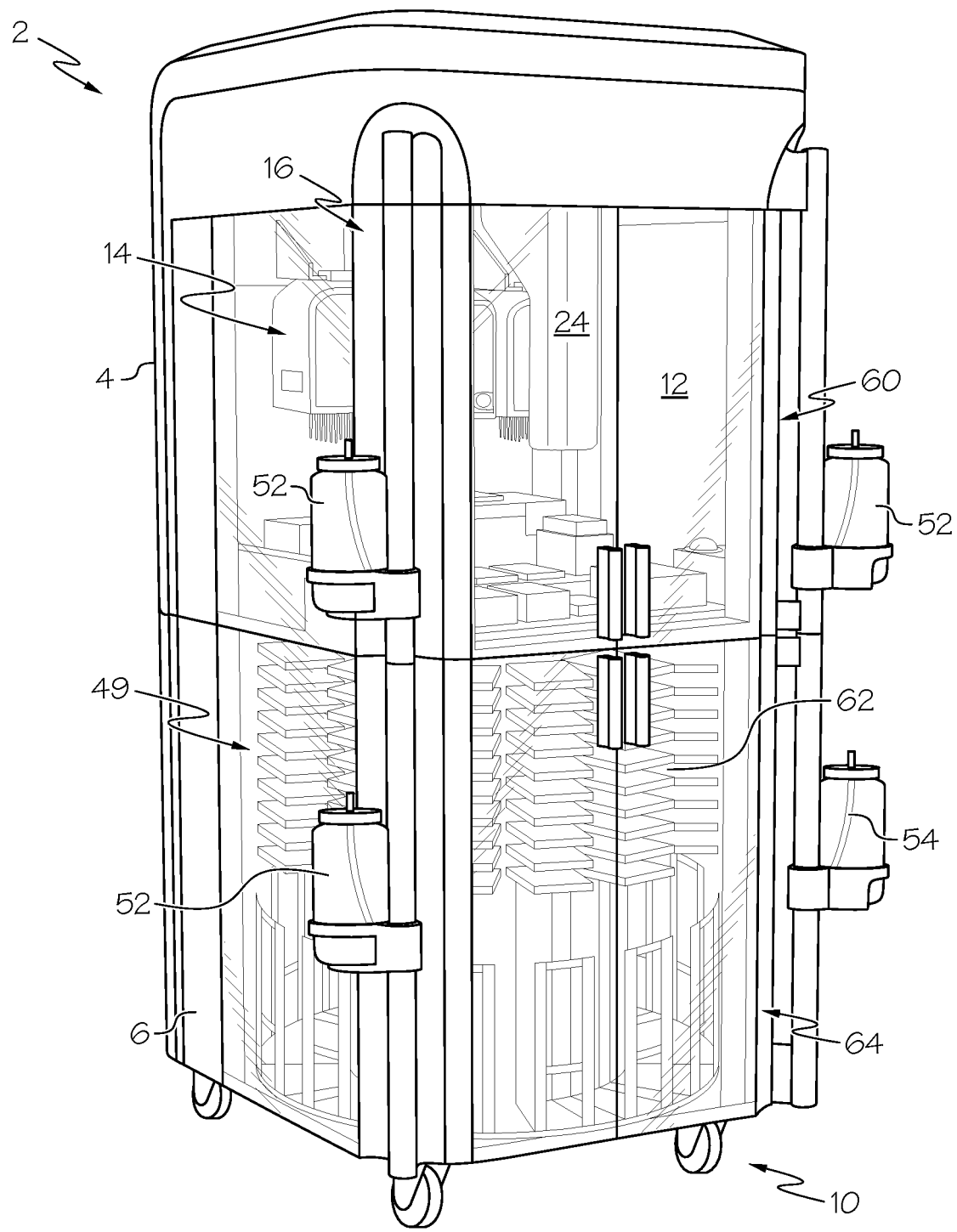
Figure 14:
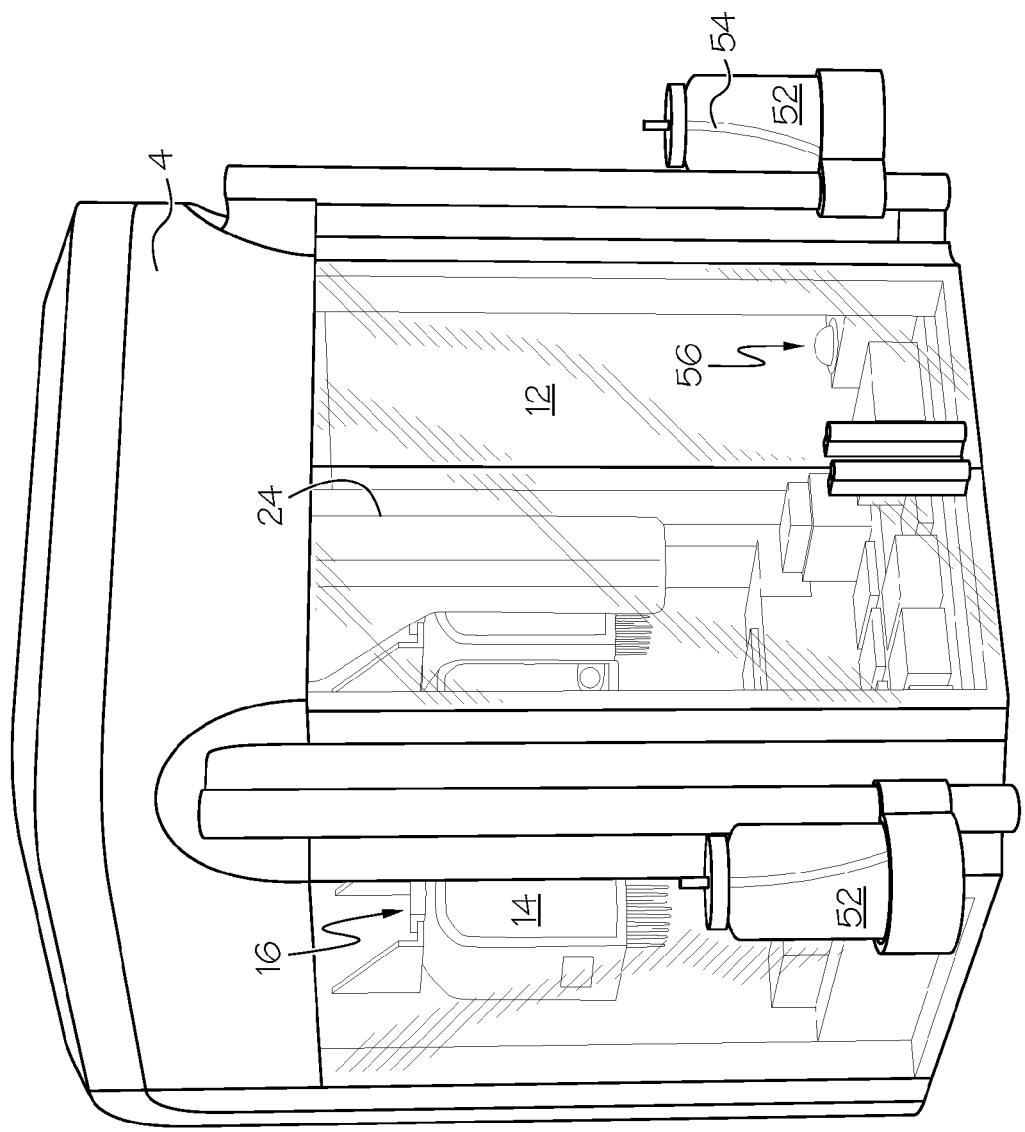
Figure 15:
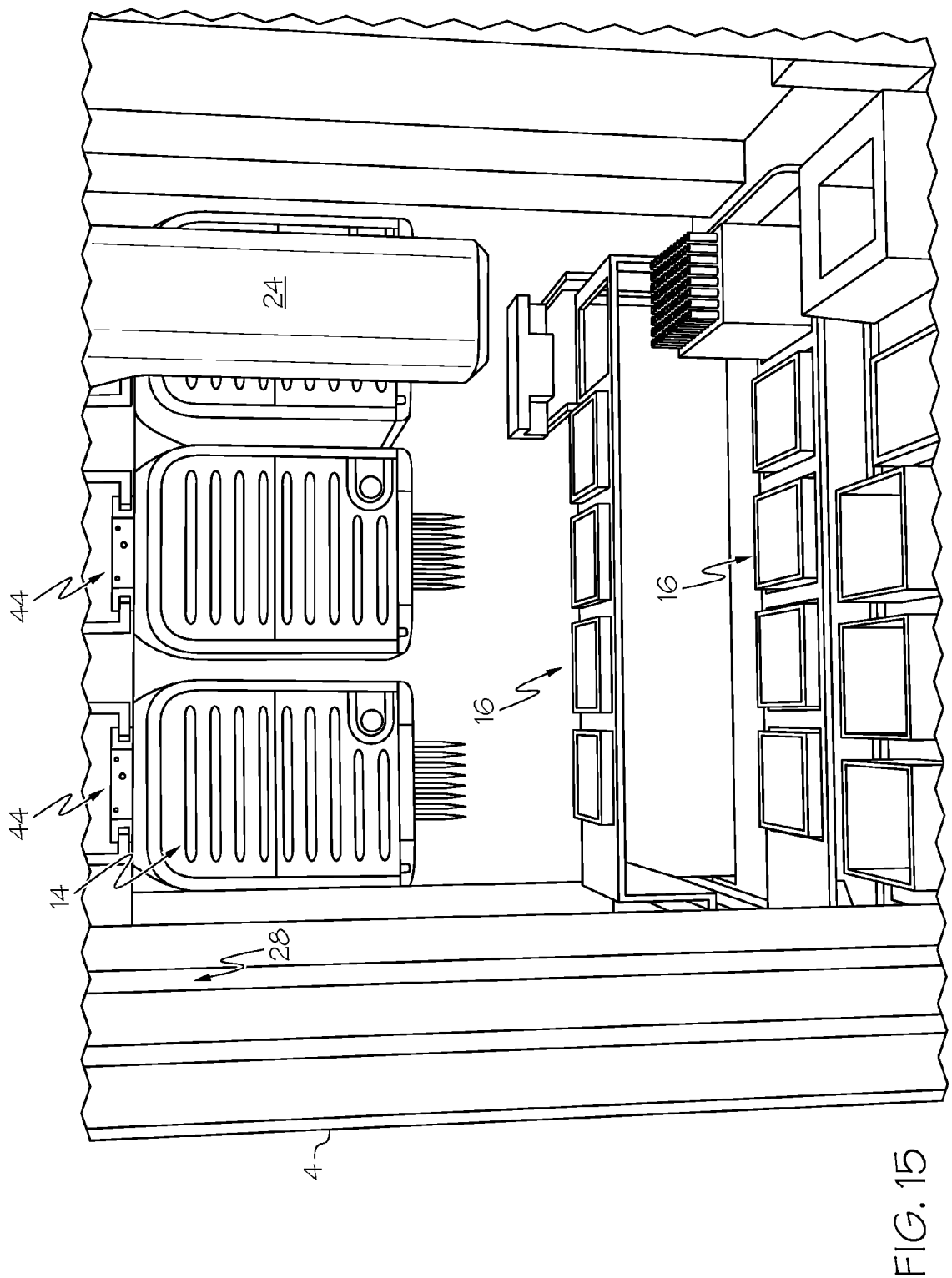
FIG. 15 shows a side perspective view of a pipetting chamber, including overhead mounted pipetting cartridges, according to various embodiments.
Figure 17:
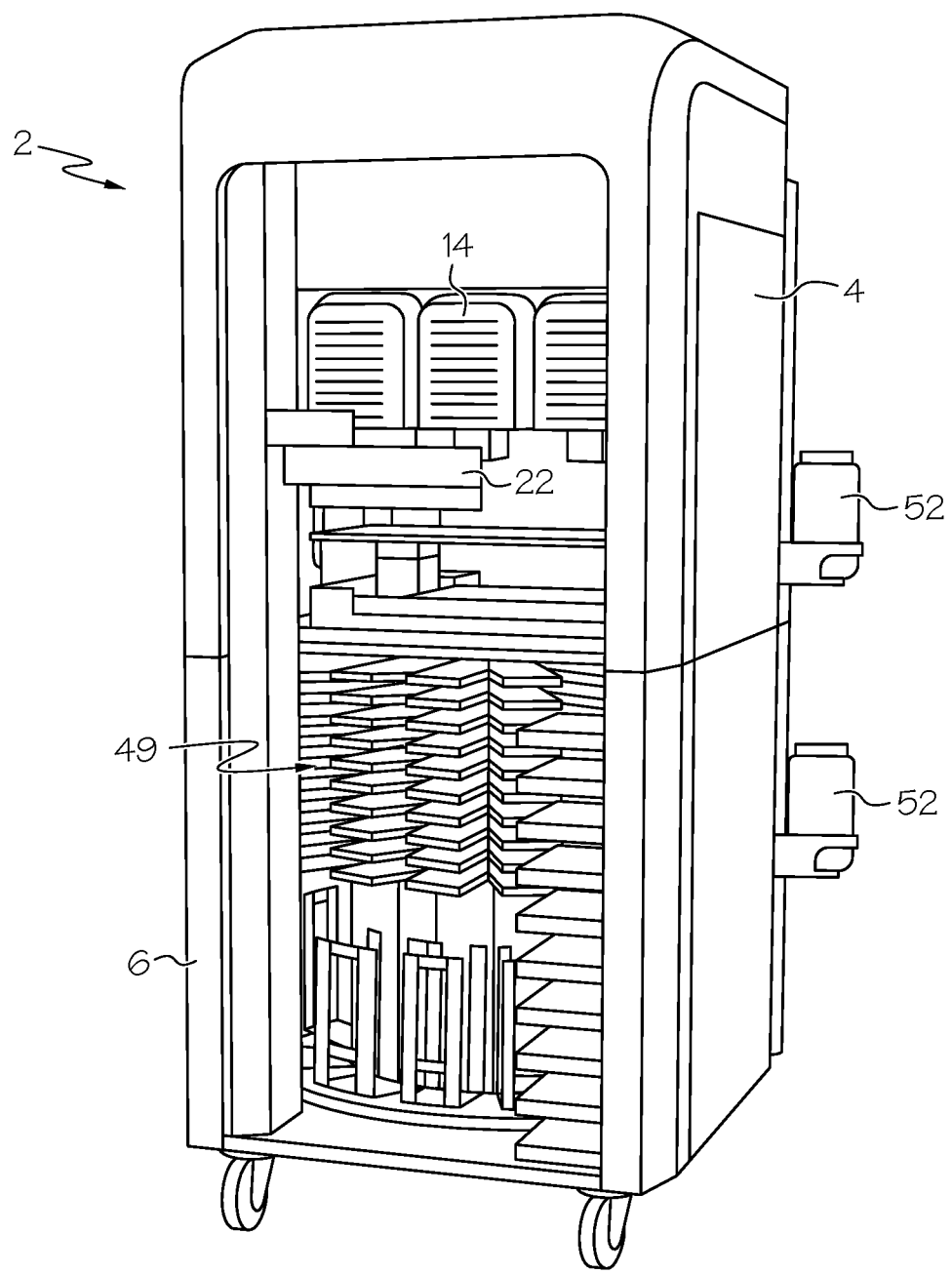
FIG. 17 shows a back perspective view of a system according to various embodiments.

The perspective views in FIGS. 11, 13, 14 and 17, for example, illustrate additional features of the system 2. For example, the system 2 can further include a set of fluid reservoirs 52 coupled with an exterior of at least one of the storage chamber 6 or the pipetting chamber 4. In some embodiments, as shown in FIG. 17, the fluid reservoirs 52 may be coupled to both the exterior of the pipetting chamber 4 and the storage chamber 6. In other embodiments, as shown in FIG. 14, where the pipetting chamber 4 is a stand-alone system, the fluid reservoirs can be coupled to the exterior of only the pipetting chamber 4. In any case, the system 2 can further include a set of fluid conduits 54, each connected with one of the set of fluid reservoirs 52 and the set of pipettor cartridge(s) 14 within the pipetting chamber 4. The fluid conduits 54 can be further connected with a pump 56 within the pipetting chamber 4, where the pump 56 pumps the fluid from the reservoir 52, through the conduits 54 to the set of pipettor cartridges 14.

Figure 12:
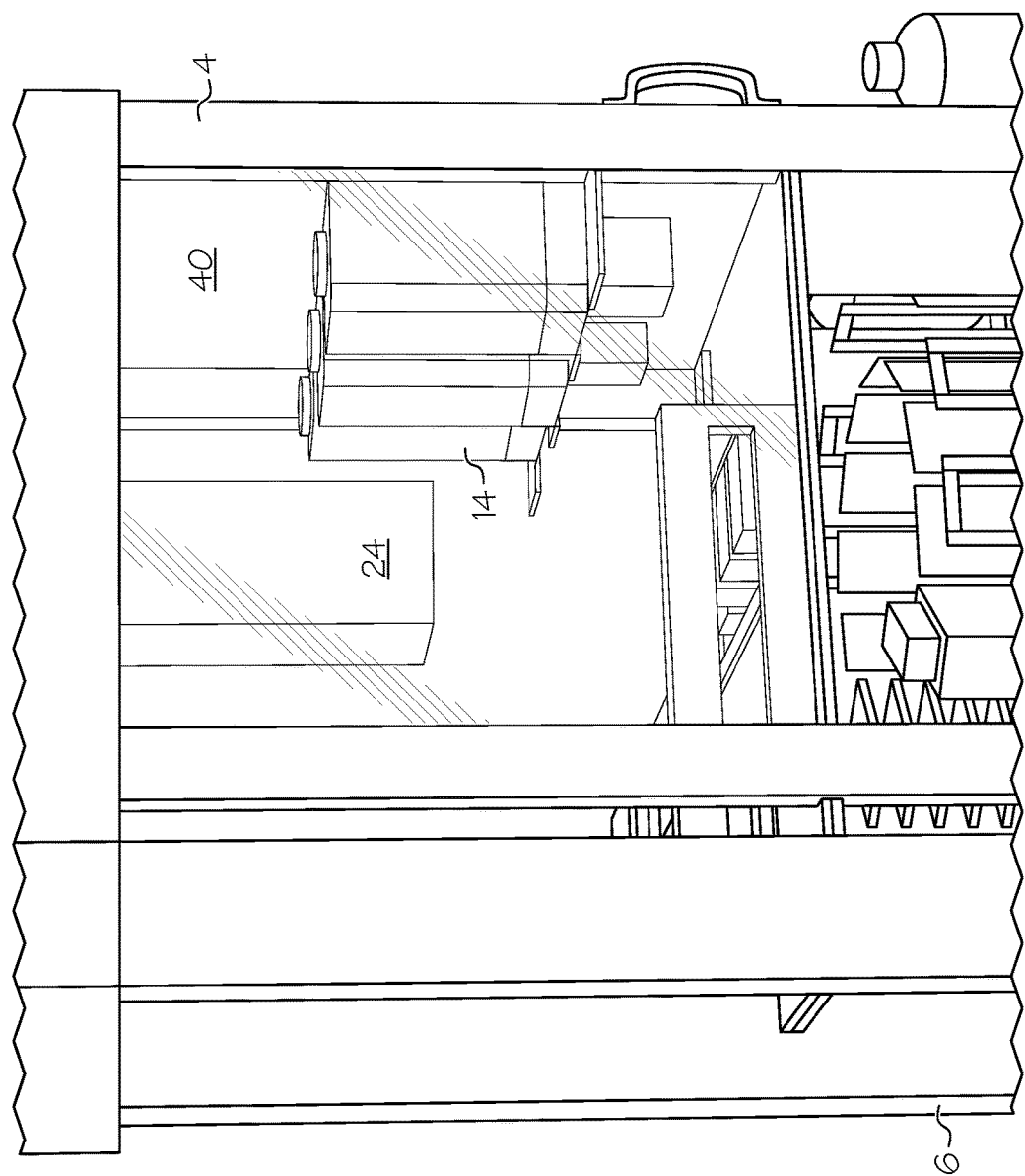
FIGS. 12-14 show perspective views of systems according to various embodiments.

The perspective views in FIGS. 12-14 show additional features of the system 2 according to various embodiments, including, for example, a first set of doors (doors 12) on a side 60 of the pipetting chamber 4 for accessing the pipetting chamber 4. Also shown, in some embodiments, the system can include a second set of doors 62 on a side 64 of the storage chamber 6 (side 64 may be shared with side 60), where the second set of doors can be used to access the stored pipetting trays 18 within the storage chamber 6.

Figure 16:
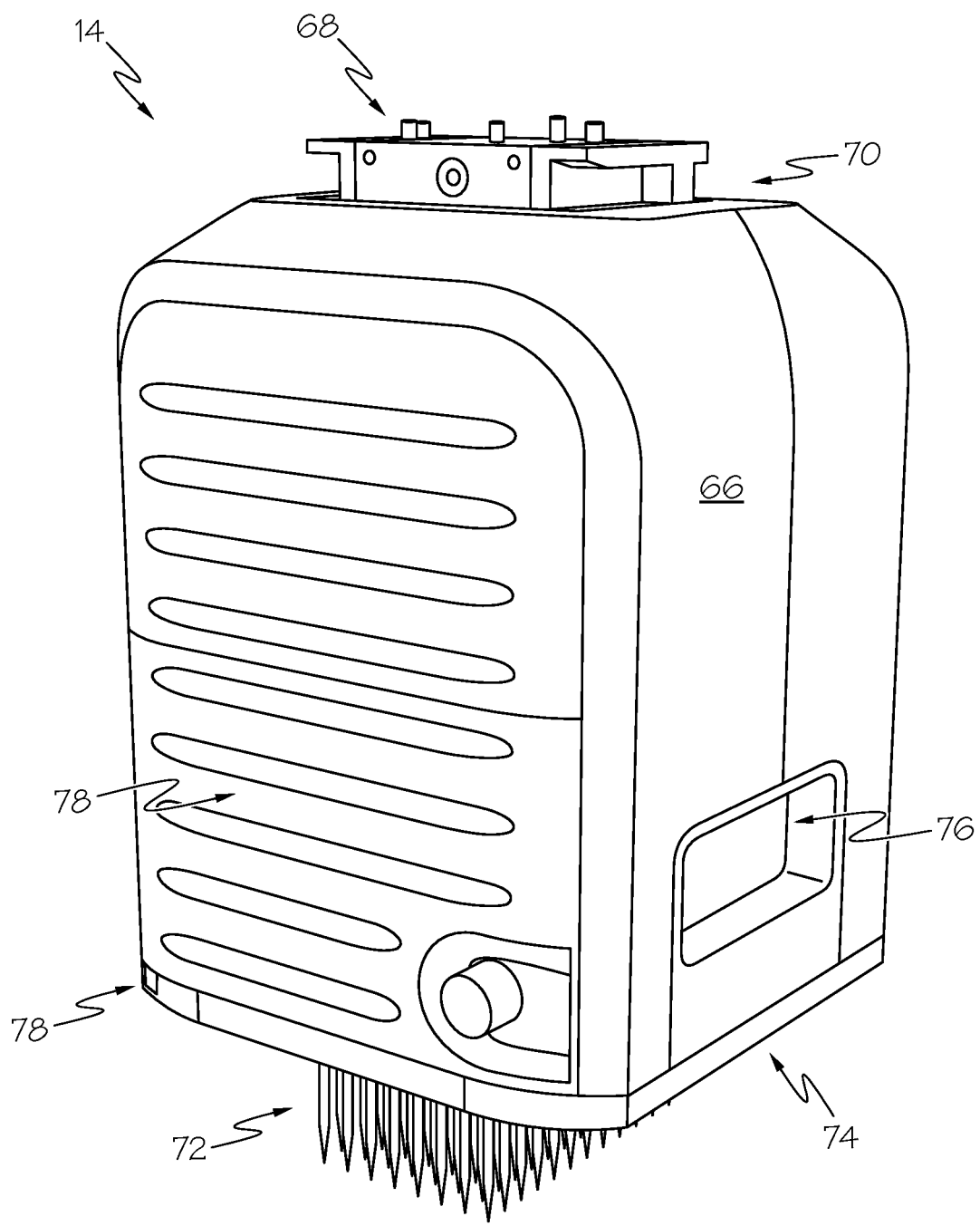
FIG. 16 shows a close-up perspective view of a pipettor cartridge according to various embodiments.

FIG. 16 shows a close-up perspective view of a pipettor cartridge 14 according to various embodiments. As shown, the pipettor cartridge 14 can include a casing 66, a mount 68 on a top side 70 of the casing 66 (for top-mounting embodiments), and a set of pipettes 72 extending from a bottom side 74 of the casing 66. The pipettor cartridge 14 can also include an access door 74 on a side of the casing 66 between the top side 70 and the bottom side 74. In various embodiments, the pipettor cartridge(s) 14 can include at least one handle 76 on the casing 66 for gripping the casing 66, and a display (e.g., a light-emitting diode (LED) or other light-based display) 78 indicating at least one of a power to the pipettor cartridge or a status of a pipetting procedure.

Figure 18:
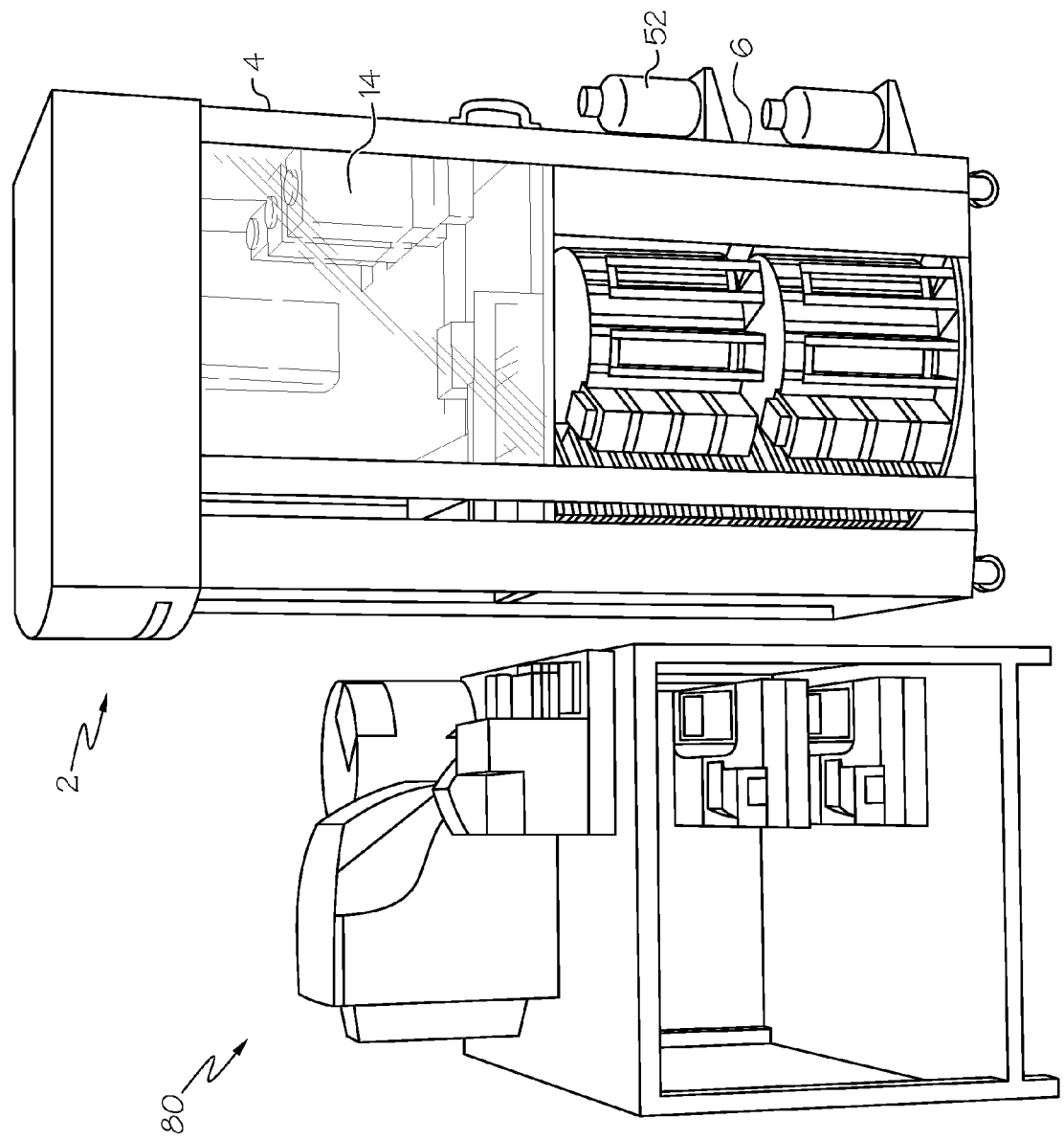
FIG. 18 shows a perspective view of a system according to various embodiments, integrated with an incubator system.
Figure 19:
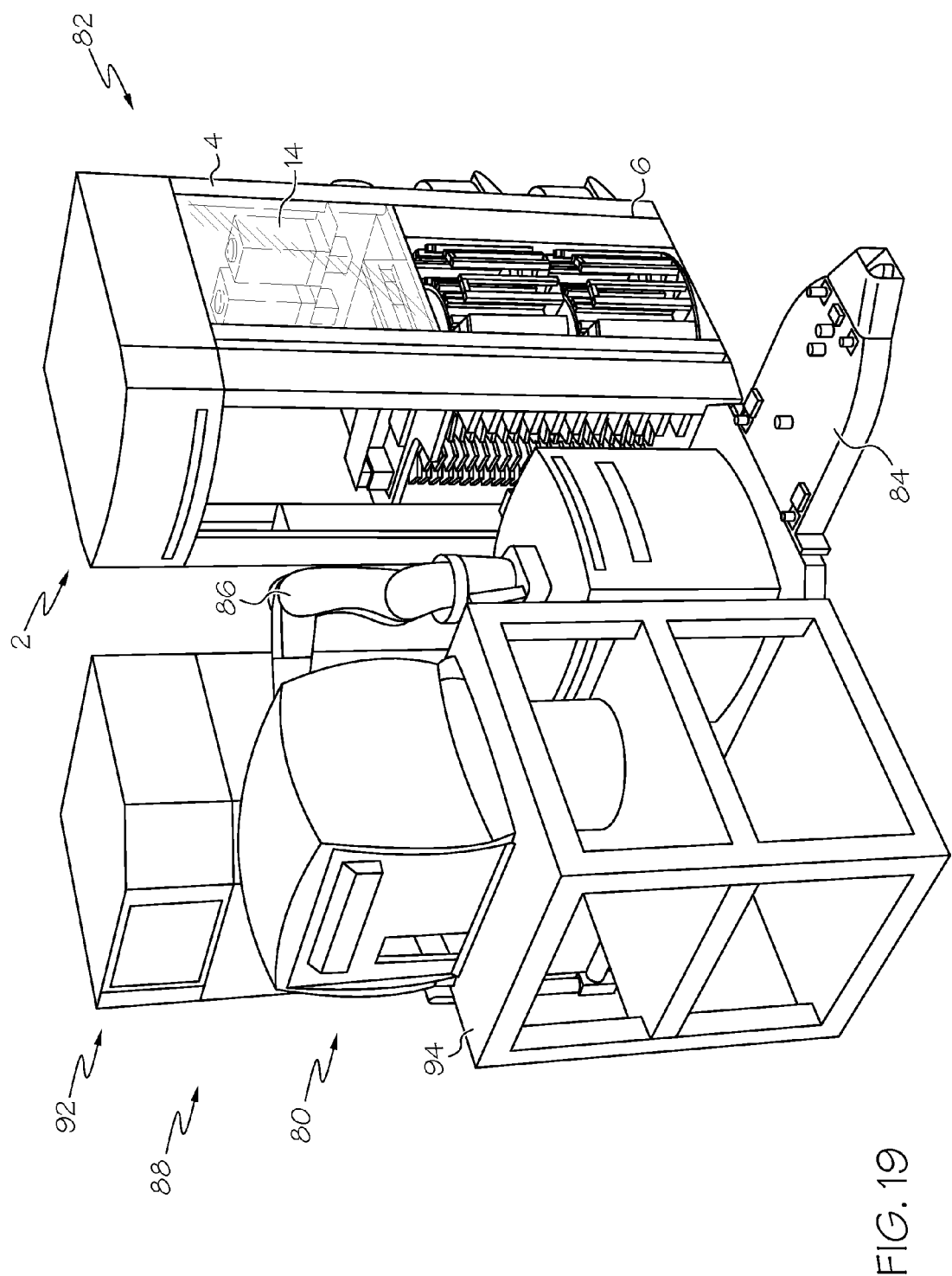
FIG. 19 shows a perspective view of a configuration including a system according to various embodiments.

FIG. 17 shows a back perspective view of the system 2, illustrating various aspects described herein. FIG. 18 shows the system 2 integrated with a supply system 80, e.g., operably connected with an incubator system 80 for incubating specimens and/or transporting specimens to/from the system 2. FIG. 19 shows a perspective view of the system 2 in a configuration 82 including a movable cart 84 with a robotic arm 86 mounted thereon. The configuration 82 can further include at least one additional system 88, which can include an incubator system 80 and/or an additional storage system 92. The configuration 82 can be designed to allow the robotic arm 86 to transport specimens, e.g., pipetting trays 18 or other liquid trays between the system 2, incubator system 80 (mounted on cart 94) and/or the additional storage system 92.

As described herein, the control system (CS) 8 can include any conventional control system components used in controlling laboratory equipment (including, e.g., pipetting chamber 4 and/or storage chamber 6). For example, the control system 8 can include electrical and/or electro-mechanical components for actuating one or more components in the pipetting chamber 4 and/or storage chamber 6. The control system 8 can include conventional computerized sub-components such as a processor, memory, input/output, bus, etc. The control system 8 can be configured (e.g., programmed) to perform functions based upon operating conditions from an external source (e.g., at least one computing device), and/or may include pre-programmed (encoded) instructions based upon parameters of the pipetting chamber 4 and/or storage chamber 6.

In various embodiments, the control system 8 is embodied, e.g., stored and/or operated in at least one computing device, which is connected with the pipetting chamber 4 and/or storage chamber 6. One or more of the processes described herein can be performed, e.g., by at least one computing device, such as control system 8, as described herein. In other cases, one or more of these processes can be performed according to a computer-implemented method. In still other embodiments, one or more of these processes can be performed by executing computer program code (e.g., control system 8) on at least one computing device, causing the at least one computing device to perform a process, e.g., controlling operation of pipetting chamber 4 and/or storage chamber 6.

In any event, control system 8 (e.g., at least one computing device) can comprise one or more general purpose computing articles of manufacture (e.g., computing devices) capable of executing program code installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, control system 8 can be embodied as any combination of system software and/or application software. In any event, the technical effect of control system 8 is to control operation of pipetting chamber 4 and/or storage chamber 6.

Further, control system 8 can be implemented using a set of modules In this case, a module can enable control system 8 to perform a set of tasks used by control system 8, and can be separately developed and/or implemented apart from other portions of control system 8. Control system 8 may include modules which comprise a specific use machine/hardware and/or software. Regardless, it is understood that two or more modules, and/or systems may share some/all of their respective hardware and/or software. Further, it is understood that some of the functionality discussed herein may not be implemented or additional functionality may be included as part of control system 8.

When control system 8 comprises multiple computing devices, each computing device may have only a portion of control system 8 embodied thereon (e.g., one or more modules). However, it is understood that control system 8 (and its computing device(s)) are only representative of various possible equivalent computer systems that may perform a process described herein. To this extent, in other embodiments, the functionality provided by computing device and control system 8 can be at least partially implemented by one or more computing devices that include any combination of general and/or specific purpose hardware with or without program code. In each embodiment, the hardware and program code, if included, can be created using standard engineering and programming techniques, respectively.

Regardless, when control system 8 includes multiple computing devices, the computing devices can communicate over any type of communications link. Further, while performing a process described herein, control system 8 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As discussed herein, control system 8 enables control of pipetting chamber 4 and/or storage chamber 6. Control system 8 may include logic for performing one or more actions described herein. In one embodiment, control system 8 may include logic to perform the above-stated functions. Structurally, the logic may take any of a variety of forms such as a field programmable gate array (FPGA), a microprocessor, a digital signal processor, an application specific integrated circuit (ASIC) or any other specific use machine structure capable of carrying out the functions described herein. Logic may take any of a variety of forms, such as software and/or hardware. However, for illustrative purposes, control system 8 and logic included therein will be described herein as a specific use machine. As will be understood from the description, while logic is illustrated as including each of the above-stated functions, not all of the functions are necessary according to the teachings of the invention as recited in the appended claims.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system comprising:
   a pipetting chamber;
   a set of pipettor cartridges docked in the pipetting chamber;
   a tray dock movably mounted within the pipetting chamber;
   a gantry system mounted on a ceiling within the pipetting chamber, the gantry system including:
      at least one stationary track aligned in a first direction, and
      a movable track aligned in a second direction distinct from the first direction, the movable track coupled to the at least one stationary track; and
   a carrier configured to transport each pipettor cartridge of the set of pipettor cartridges to a pipetting location within the pipetting chamber, the carrier configured to move each pipettor cartridge in a third direction perpendicular to both the first and second directions;
   wherein the tray dock is movable within the pipetting chamber relative to the pipetting location, the tray dock including more than one tray dock sections each being separate and distinct from each other and each of the more than one tray dock sections being configured for docking with a different corresponding pipetting tray and each of the more than one tray dock sections being moved past each other relative to the pipetting location so as to swap the different corresponding pipetting trays at the pipetting location.

2. The system of claim 1, further comprising an arm coupled to the tray dock for moving the tray dock in each of the first direction, the second direction, and the third direction.

3. The system of claim 1, further comprising a storage chamber coupled to the pipetting chamber, the storage chamber for storing pipetting trays.

4. The system of claim 3, wherein the storage chamber includes a storage carousel for storing the pipetting trays.

5. The system of claim 4, wherein the storage chamber includes a robotic arm configured to move the pipetting trays between the pipetting chamber and the storage chamber.

6. The system of claim 3, further comprising:
   a set of fluid reservoirs coupled with an exterior of at least one of the storage chamber or the pipetting chamber; and
   a set of fluid conduits fluidly connected with the set of fluid reservoirs and the set of pipettor cartridges through the pipetting chamber.

7. The system of claim 6, further comprising a pump within the pipetting chamber, the pump fluidly connected with the set of fluid conduits, the pump for pumping fluid from the set of fluid reservoirs to the set of pipettor cartridges.

8. The system of claim 3, wherein the storage chamber is located below the pipetting chamber.

9. The system of claim 8, further comprising:
a first set of doors on a side of the pipetting chamber for accessing the pipetting chamber; and
a second set of doors on a side of the storage chamber shared with the side of the pipetting chamber, the second set of doors for accessing the stored pipetting trays.

10. The system of claim 1, wherein each pipettor cartridge of the set of pipettor cartridges includes:
a casing;
a mount on a top side of the casing;
a set of pipettes extending from a bottom side of the casing; and
an access door on a side of the casing between the top side and the bottom side.

11. The system of claim 10, wherein each pipettor cartridge of the set of pipettor cartridges further includes:
at least one handle on the casing for gripping the casing; and
a display indicating at least one of power to the pipettor cartridge or a status of a pipetting procedure.

12. The system of claim 1, wherein the carrier is further configured to rotate about an axis of the carrier to at least one of engage a pipettor cartridge, disengage a pipettor cartridge or facilitate pipetting via a pipettor cartridge, wherein the axis of the carrier is parallel to the third direction.

13. The system of claim 1, wherein the at least one stationary track includes two distinct stationary tracks aligned in parallel, the two distinct stationary tracks aligned perpendicular to the movable track.

14. The system of claim 1, wherein the set of pipettor cartridges is docked to the ceiling of the pipetting chamber.

15. The system of claim 1, wherein the set of pipettor cartridges is docked in a docking station within the pipetting chamber.

16. The system of claim 1, wherein the more than one tray dock sections are disposed within the pipetting chamber to move freely past each other and a pipettor cartridge on the carrier at the pipetting location and swap the different corresponding pipetting trays at the pipetting location.

17. The system of claim 1, wherein the gantry system is configured so that the carrier moves freely in the first, second and third directions between the pipetting location and different docking locations of the set of pipettor cartridges effecting replacement at the pipetting location of a pipettor cartridge of the set of pipettor cartridges with another pipettor cartridge of the set of pipettor cartridges independent of tray dock section movement swapping the different corresponding pipettor trays at the pipetting location.

18. The system of claim 1, wherein each tray dock section is configured so as to be moved past each other tray dock section relative to an opening location of a tray passage opening between a storage chamber and the pipettor chamber, the opening location being away from the pipetting location, so as to swap the different corresponding pipetting trays at the opening location, wherein the storage chamber is coupled to the pipetting chamber.

19. The system of claim 1, wherein at least a corresponding pipetting tray docked to one of the more than one tray dock sections is of a different type than another corresponding pipetting tray docked to another of the more than one tray dock sections.

20. The system of claim 18, wherein the more than one tray dock sections include a number of tray dock sections so that swapping movement of tray dock section is effected at the pipetting location with a tray dock section located at the opening location.

21. The system of claim 18, wherein the more than one tray dock sections include a number of tray dock sections so that swapping movement of tray dock section is effected at the opening location with a tray dock section located at the pipetting location.

22. A system comprising:
a pipetting chamber having a ceiling within the pipetting chamber;
a set of pipettor cartridges docked on the ceiling within the pipetting chamber;
a tray dock movably mounted within the pipetting chamber;
a gantry system mounted on the ceiling within the pipetting chamber, the gantry system including:
at least one stationary track aligned in a first direction, and
a movable track aligned in a second direction distinct from the first direction, the movable track coupled to the at least one stationary track;
a carrier configured to transport each pipettor cartridge of the set of pipettor cartridges to a pipetting location within the pipetting chamber, the carrier configured to move each pipettor cartridge in a third direction perpendicular to both the first and second directions; and
a control system coupled with the pipetting chamber, the control system for controlling movement of the carrier along the first direction, the second direction and the third direction;
wherein the tray dock is movable within the pipetting chamber relative to the pipetting location, the tray dock including more than one tray dock sections each being separate and distinct from each other and each of the more than one tray dock sections being configured for docking with a different corresponding pipetting tray and each of the more than one tray dock sections being moved past each other relative to the pipetting location so as to swap the different corresponding pipetting trays at the pipetting location.

23. The system of claim 22, wherein each pipettor cartridge of the set of pipettor cartridges includes:
a casing;
a mount on a top side of the casing;
a set of pipettes extending from a bottom side of the casing; and
an access door on a side of the casing between the top side and the bottom side.

24. The system of claim 22, wherein the carrier is further configured to rotate about an axis of the carrier to at least one of engage a pipettor cartridge, disengage a pipettor cartridge or facilitate pipetting via a pipettor cartridge, wherein the axis of the carrier is parallel to the third direction.

25. The system of claim 22, further comprising a storage chamber coupled to the pipetting chamber, the storage chamber for storing pipetting trays.

26. The system of claim 25, further comprising:
a set of fluid reservoirs coupled with an exterior of at least one of the storage chamber or the pipetting chamber; and a set of fluid conduits fluidly connected with the set of fluid reservoirs and the set of pipettor cartridges through the pipetting chamber.

27. The system of claim 25, wherein the storage chamber includes a storage carousel for storing the pipetting trays, wherein the storage chamber includes a robotic arm configured to move the pipetting trays between the pipetting chamber and the storage chamber.

28. The system of claim 27, wherein the robotic arm is configured to move the pipetting trays between the pipetting chamber and the storage chamber in a Z direction, and is configured to move the pipetting trays in X and Y directions within each of the pipetting chamber and the storage chamber.

29. The system of claim 22, wherein the more than one tray dock sections are disposed within the pipetting chamber to move freely past each other and a pipettor cartridge on the carrier at the pipetting location and swap the different corresponding pipetting trays at the pipetting location.

30. The system of claim 22, wherein the gantry system is configured so that the carrier moves freely in the first, second and third directions between the pipetting location and different docking locations of the set of pipettor cartridges effecting replacement at the pipetting location of a pipettor cartridge of the set of pipettor cartridges with another pipettor cartridge of the set of pipettor cartridges independent of tray dock section movement swapping the different corresponding pipettor trays at the pipetting location.

31. The system of claim 22, wherein each tray dock section is configured so as to be moved past each other tray dock section relative to an opening location of a tray passage opening between a storage chamber and the pipettor chamber, the opening location being away from the pipetting location, so as to swap the different corresponding pipetting trays at the opening location, wherein the storage chamber is coupled to the pipetting chamber.

32. The system of claim 22, wherein at least a corresponding pipetting tray docked to one of the more than one tray dock sections is of a different type than another corresponding pipetting tray docked to another of the more than one tray dock sections.

33. The system of claim 31, wherein the more than one tray dock sections include a number of tray dock sections so that swapping movement of tray dock section is effected at the pipetting location with a tray dock section located at the opening location.

34. The system of claim 31, wherein the more than one tray dock sections include a number of tray dock sections so that swapping movement of tray dock section is effected at the opening location with a tray dock section located at the pipetting location.

35. A system comprising:
a pipetting chamber having a ceiling within the pipetting chamber;
a set of pipettor cartridges docked on the ceiling within the pipetting chamber;
a tray dock movably mounted within the pipetting chamber;
a gantry system mounted on the ceiling within the pipetting chamber, the gantry system including:
at least one stationary track aligned in a first direction, and
a movable track aligned in a second direction distinct from the first direction, the movable track coupled to the at least one stationary track; and
a carrier configured to transport each pipettor cartridge of the set of pipettor cartridges to a pipetting location within the pipetting chamber, the carrier configured to move each pipettor cartridge in a third direction perpendicular to both the first and second directions, wherein the carrier is further configured to move completely circumferentially about the set of pipettor cartridges docked on the ceiling; and
a control system coupled with the pipetting chamber, the control system for controlling movement of the carrier along the first direction, the second direction and the third direction;
wherein the tray dock is movable within the pipetting chamber relative to the pipetting location, the tray dock including more than one tray dock sections each being separate and distinct from each other and each of the more than one tray dock sections being configured for docking with a different corresponding pipetting tray and each of the more than one tray dock sections being moved past each other relative to the pipetting location so as to swap the different corresponding pipetting trays at the pipetting location.

36. The system of claim 35, comprising a robotic arm configured to move the different corresponding pipetting trays between the pipetting chamber and a storage chamber in a Z direction, and is configured to move the pipetting trays in X and Y directions within each of the pipetting chamber and the storage chamber.

37. The system of claim 35, wherein the more than one tray dock sections are disposed within the pipetting chamber to move freely past each other and a pipettor cartridge on the carrier at the pipetting location and swap the different corresponding pipetting trays at the pipetting location.

38. The system of claim 35, wherein the gantry system is configured so that the carrier moves freely in the first, second and third directions between the pipetting location and different docking locations of the set of pipettor cartridges effecting replacement at the pipetting location of a pipettor cartridge of the set of pipettor cartridges with another pipettor cartridge of the set of pipettor cartridges independent of tray dock section movement swapping the different corresponding pipettor trays at the pipetting location.

39. The system of claim 35, wherein each tray dock section is configured so as to be moved past each other tray dock section relative to an opening location of a tray passage opening between a storage chamber and the pipettor chamber, the opening location being away from the pipetting location, so as to swap the different corresponding pipetting trays at the opening location, wherein the storage chamber is coupled to the pipetting chamber.

40. The system of claim 35, wherein at least a corresponding pipetting tray docked to one of the more than one tray dock sections is of a different type than another corresponding pipetting tray docked to another of the more than one tray dock sections.

41. The system of claim 39, wherein the more than one tray dock sections include a number of tray dock sections so that swapping movement of tray dock section is effected at the pipetting location with a tray dock section located at the opening location.

42. The system of claim 39, wherein the more than one tray dock sections include a number of tray dock sections so that swapping movement of tray dock section is effected at the opening location with a tray dock section located at the pipetting location.

\* \* \* \* \*